United States Patent [19]

Timms

[11] Patent Number: 4,481,145

[45] Date of Patent: Nov. 6, 1984

[54] DISPROPORTIONATION OF UNSATURATED ACIDS

[75] Inventor: Donald G. Timms, Hilly Ground, England

[73] Assignee: Enichem Elastomers Limited, Southhampton, England

[21] Appl. No.: 462,451

[22] Filed: Jan. 31, 1983

[30] Foreign Application Priority Data

Feb. 1, 1982 [GB] United Kingdom ............... 8202844

[51] Int. Cl.$^3$ ........................... C09F 1/04; C09F 7/08
[52] U.S. Cl. ............................... 260/405.6; 260/407; 260/97; 260/97.5; 585/531
[58] Field of Search ................. 260/407, 405.6, 97, 260/97.5; 585/531

[56] References Cited

U.S. PATENT DOCUMENTS

| | | | |
|---|---|---|---|
| 2,411,111 | 11/1946 | Ralston et al. | 260/405.6 |
| 3,076,003 | 1/1963 | Meyers et al. | 260/407 |
| 3,257,377 | 6/1966 | Hannah et al. | 260/407 X |
| 3,277,072 | 10/1966 | Patrick et al. | 260/97 |
| 3,374,217 | 3/1968 | Summers et al. | 260/97 X |
| 3,786,037 | 1/1974 | Krause | 260/97.5 |
| 3,872,073 | 3/1975 | Thorpe et al. | 260/97.5 X |
| 3,923,768 | 12/1975 | Powers et al. | 260/97.5 |
| 3,980,630 | 9/1976 | Ishigami et al. | 260/97.5 X |
| 4,259,459 | 3/1981 | Force | 260/97.5 X |
| 4,265,807 | 5/1981 | Breslow | 260/97 X |
| 4,271,066 | 6/1981 | Matsuo et al. | 260/97 X |

FOREIGN PATENT DOCUMENTS

| | | |
|---|---|---|
| 1398926 | 6/1975 | United Kingdom . |
| 2060637 | 5/1980 | United Kingdom . |

*Primary Examiner*—Thomas A. Waltz
*Attorney, Agent, or Firm*—Cushman, Darby & Cushman

[57] ABSTRACT

Unsaturated acids in rosin or tall oil are disproportionated by heating the rosin or tall oil with a catalyst comprising iodine and an iron compound using ammonia, an ammonium salt or an amine as an additional component of the catalyst. Use of this additional component gives a remarkable and unexpected increase in reaction rate and enables the preparation of a disproportionated rosin containing 0.5% or less residual abietic acid, as measured by ultraviolet spectroscopy.

8 Claims, No Drawings

DISPROPORTIONATION OF UNSATURATED ACIDS

This invention relates to the disproportionation of unsaturated acids in rosin or tall oil.

Rosin consists of about 90% or more of mixed unsaturated acids. These are mainly isomeric rosin acids ($C_{19}H_{29}COOH$) but, in some cases, such as in tall oil rosin, a considerable proportion of fatty acids, mainly oleic and linoleic acid, is present as well. The composition of rosins from various sources (oleo rosin, gum rosin, wood rosin and tall oil rosin) is quoted in "Modern Surface Coatings" Paul Nylen et al, Interscience Publishers 1965, pages 133-137 and in particular in Table 4.22-2 on page 136. Rosin and rosin derivatives are also discussed in Encyclopedia of Chemical Technology, Volume 11, Interscience Publishers 1953, pages 779-810. One important use for rosin derivatives is as an emulsifier for free radical emulsion polymerisation processes. It is well known that crude, unmodified rosin is not suitable for such purposes since it contains a high proportion of abietic acid type acids (abietic, neoabietic and palustric acids). The conjugated double bond in these acids interferes with the polymerisation reaction. Processes for modifying the crude rosin to remove such acids are well known.

Disproportionation is the preferred process carried out on a commercial scale. In the disproportionation reaction abietic acid and other acids containing a conjugated dienic function are converted to di- and tetrahydroabietic acid and dehydroabietic acid. If rosin so treated is to be used for the manufacture of soaps suitable for emulsion polymerisation processes, it is essential to reduce the level of abietic acid to below 1% (by weight) preferably to 0.5% or less, as measured by ultraviolet spectroscopy.

It is well known that iodine can effect disproportionation of rosin but, by itself it is of little value as a catalyst as the reaction needs to be conducted for a considerable length of time at high temperatures. Under these conditions appreciable decomposition occurs. Moreover, appreciable amounts of abietic acid may remain and the product may have a low softening point, poor colour and low potash number. The disproportionation reaction using iodine can be greatly improved if a multi valent metal or metal compound is employed as a co-catalyst, for example compounds of iron, copper, cobalt, manganese or tin. These metals are conveniently added as halides or carboxylic acid salt although other compounds, such as the respective acetyl acetonate, may be used. However, if the rosin is to be used for the manufacture of synthetic polymer latices it is desirable to exclude metals such as copper, cobalt or manganese.

In our British patent application No. 2060637 we have described a process for the disproportionation of unsaturated acids in rosin or tall oil by heating with a catalyst comprising iodine and iron chloride or iron bromide. We have examined the activity of the system iodine—iron compound, using ferric chloride as the preferred source of iron on the grounds of cheapness, availability and ready solubility in molten rosin. With, for example, 0.2 parts ferric chloride hydrate and 0.3 parts iodine per hundred parts of rosin (all parts by weight) the disproportionation reaction proceeds smoothly within the temperature range 210°-260° C. and at 230° C. reaction is complete at the end of 3 hours. Residual abietic acid is about 0.8% measured by gas chromatography, but analysis of the product using ultra violet spectroscopy indicates the presence of other, as yet unidentified, dienic compounds in small amounts. Analysis using gas chromatography also reveals the presence of small but significant amounts of low molecular weight compounds not present in the starting rosin. Batches of disproportionated rosin made in this way have been tested for their suitability in styrene butadiene rubber (SBR 1500) latex polymerisations and through satisfactory in most instances, occasionally some slowing down of the polymerisation rate has been observed, indicating that the disproportion is only marginally effective. A secondary problem with rosin made by this process is its somewhat low softening point, which can make flaking and subsequent storage difficult under warm ambient conditions. We have noted that similar problems occur if a carboxylic acid salt of iron, or iron bromide, is used as the source of iron. Sodium carbonate or potassium carbonate is known to raise the softening point and therefore the effect of adding small amounts of sodium carbonate before the addition of the catalyst components was examined. Although a product of somewhat higher softening point is obtained, no other effect on the reaction was observed.

To our surprise, when ammonium carbonate (a mixture of carbonate and carbamate) was tried as a third component a product of higher softening point was obtained accompanied by a quite unexpected and remarkable increase in the reaction rate. Reaction was complete within 15 minutes of the temperature reaching 220° C. instead of the usual 2 to 3 hours. Furthermore the product contained only 0.5% abietic acid and when tested in an SBR 1500 type emulsion polymerisation recipe was found to be comparable with high quality commercial material.

Further experiments showed that if ammonia or an amine was used as a third catalyst component, the amount of iron could be greatly reduced, as little as 50 ppm (as Fe) being sufficient for disproportionation to be complete within one hour at 220° C. Even smaller amounts of iron were found to be effective, though with levels around 10 ppm it was observed that the softening point of the product decreased. It may be noted that raw rosin contains some iron, typical levels being 5 to 10 ppm in light grades and up to 50 ppm in darker grades. Thus the starting material may contain sufficient iron without the need for any further addition.

According to the present invention a process for the disproportionation of unsaturated acids in rosin or tall oil by heating the rosin or tall oil with a catalyst comprising iodine and an iron compound is characterised by the use of ammonia, an ammonium salt or an amine as an additional component of the catalyst. For simplicity the term "rosin" is used hereafter to include tall oil unless the context indicates otherwise.

The amount of iodine employed is at least 0.01% based on the weight of rosin and is preferably at least 0.1% since below this level the reaction may fail to go to completion. From experiments with different grades of rosin it is inferred that some of the iodine is involved in side reactions which make it unavailable for the desired disproportionation reaction. Taking this and volatilisation losses into account it is prudent to use 0.3-0.4% of iodine to ensure completeness of reaction in reasonable time. Larger amounts may be used, the upper limit being dictated by considerations of economy and the need to ensure that undue contamination of the product does not occur.

The amount of iron compound used is preferably in the range 0.001-0.01% contained Fe, taking into account the iron that may be present in the raw rosin. Amounts outside this range may be used, depending on what level of residual iron may be tolerated or, as mentioned, what softening point range is desired. Choice of iron compound used is determined by considerations of cost, convenience and whether residues are important in a particular application. The latter point can be dealt with by using the iron salt of a rosin, naphthenic or fatty acid. However as small amounts of chloride residues can be tolerated, ferric chloride hydrate may be preferred on grounds of cost and convenience in handling.

The ammonia or amine may be added as a gas, liquid or solid, as free base or a compound e.g. the salt of an inorganic or organic acid. Materials that have proved to be catalytically active include ammonium carbonate, urea, dimethyl and tetramethyl urea, ethylene diamine, diethylene triamine, alkanolamines and ammonium chloride. Urea is a particularly convenient material to use as it is cheap, readily available, odourless and non-toxic. The amount of ammonia or amine required is very small, e.g. 0.005-0.1%, by weight though amounts outside this range may be used.

It is not necessary to use the catalyst components in specific molar ratios, nor is it necessary to add them in any special order, though it is convenient to add the iodine last so that the reactor can be closed to prevent loss. In adding the iodine it is desirable that the temperature of the rosin should be below 150° C., preferably 120°-140° C. to avoid losses due to sublimation. Elevated temperatures are used for the disproportionation reaction, for example, 100° C. to 300° C., preferably 200° C. to 300° C., more preferably 200° to 260° C.

The reaction is preferably conducted under an atmosphere of an inert gas such as steam, carbon dioxide or nitrogen. The reactor may be vented but should not be vigorously purged during the reaction as this may cause loss of iodine. When the desired level of disproportionation is achieved the product may be treated with oxalic acid to remove excess iodine and improve the colour.

This catalyst system appears to be highly efficient in the usage of the hydrogen present in the rosin as the percentage of dehydroabietic acid is lower than is found in disproportionated rosins made using sulphur or supported metal catalysts.

The catalyst can also be used to reduce the conjugated diene content of fatty-rosin acid mixtures derived from Tall Oil, and polyunsaturated fatty acids.

The invention includes a process for producing an emulsifier by neutralising the product of the disproportionation reaction. It also includes the emulsion polymerisation of a conjugated diene, optionally with one or more comonomers (eg a vinyl aromatic such as styrene) and especially the preparation of SBR latex or solid rubber, employing an emulsifier so prepared.

Some preferred embodiments of the process of the present invention will now be described by way of example.

EXAMPLE 1

(Comparative)

500 g of tree rosin were heated to 125° C. in a multi-necked glass reactor of 700 ml capacity. 1.0 g ferric chloride hydrate were added with rapid stirring and after 10 minutes 1.5 g iodine were added. The reactor was flushed with nitrogen then sealed. A vent tube was provided which terminated in an attachment flushed with nitrogen. The purpose of this vent pipe was to relieve pressure without disturbing the atmosphere above the rosin. The reactor was wrapped around with metal foil to maintain reasonable uniformity of temperature and heated to 230±5° C. At the end of 3 hours the reaction was complete as shown by analysis of samples taken at this time and later. The reaction was incomplete after 2 hours.

The product contained 0.8% abietic acid, some other dienic compounds as noted above and small amounts of low molecular weight compounds.

EXAMPLE 2

The experiment described was repeated with the addition initially of 0.6 g ammonium carbonate. With the same heating the temperature rose sharply to 245° C. then declined after 20 minutes. Samples taken at 15 minutes, 30 minutes and 1 hour from the time the temperature reached 230° C. all showed a residual abietic acid content of 0.5%. The product contained only traces of low molecular weight compounds and had a softening point 6° C. higher than the previous product.

EXAMPLE 3

In a further experiment the quantities of each catalyst ingredient were halved. After heating for 2 hours at 230° C.±5° C. the residual abietic level was 0.5%. The reaction was incomplete at the end of 1 hour.

EXAMPLE 4

Using 500 g rosin, 0.2 g ammonium carbonate, 0.33 g ferric chloride hyrdate and 1.0 g iodine, the reaction was conducted at 240° C.for 2 hours, at the end of which time the abietic acid content was 0.5%. The product was similar to that of example (2) except that the colour was lighter after bleaching. Bleaching was carried out by adding 3 g oxalic acid hydrate to the disproportionated rosin at a temperature of 170°-180° C.

EXAMPLES 5-17

Reactions were carried out in a flanged glass reactor of 700 ml capacity, equipped with an anchor stirrer, thermometer, sampling point and vent pipe. The reactor could be sparged with inert gas if required via the vent pipe. Heating was provided by an electric heating mantle equipped with an energy regulator.

In order to prevent condensation of water and other volatile materials onto the lid of the reactor, the upper parts of the apparatus were shrouded in aluminium foil and heated with air from a hot air drier.

Analysis of products was by UV spectrometry and gas chromatography. The reactor was charged with lump rosin which was heated and stirred at 160°-170° C. to remove moisture together with some of the volatile oils. The rosin was then allowed to cool to 130°-140° C. and catalyst components added. The usual order of addition was iron compound (if required), ammonia or amine source and, finally, iodine. The charge was then heated to the desired temperature and sampled at intervals to study the course of the reaction.

The product was allowed to cool to 160°-170° C. then treated with 3 grams of oxalic acid to destroy the catalyst. Stirring was continued for approximately 30 minutes and temperature maintained to remove moisture and ensure decomposition of the oxalic acid then the product was cast into dishes for further testing as required.

The residual abietic acid content (% by weight) was measured using ultraviolet spectroscopy and is given in the table. The table also shows the weight of iron (as Fe), amine or ammonium salt and iodine, together with the iron compound and amine or ammonium salt used, and the reaction conditions.

The catalyst system was also tried with samples of mixed Tall Oil rosin—fatty acid mixtures using the same apparatus and general procedure. Analysis was by gas chromatography as UV analysis was complicated by the presence of the many components of the mixtures. It was shown that the abietic acid level could be reduced to less than 0.4% and, as important, linoleic—linolenic acids could be reduced to less than 1%.

| Ex. No. | Fe (gm) | Fe addn | Amine (gm) | $I_2$ (gm) | T °C. | Time hrs. | Abietic acid % |
|---|---|---|---|---|---|---|---|
| 5 | 0.2 | $FeCl_3.6H_2O$ | — | 1.5 | 230 | 3 | 1.1% (UV)** |
| 6 | " | " | $NH_4$ carbonate 0.6 gm | 1.5 | 230 (exotherm to 256) | ¼ | 0.5 |
| 7 | 0.1 | " | $NH_4$ carbonate 0.3 g | 0.75 | 230–240 | 3 | 0.5 |
| 8 | 0.066 | " | urea 0.12 g | 1.0 | 230 exotherm to 253° C. | 1 | 0.4 |
| 9 | 0.066 | " | $K_2CO_3$ 0.26 g | 1.0 | 230 | 5 | 2 |
| 10 | 0.066 | " | $NH_4Cl$ 0.2 g | 1.0 | 245–250 | 1½ | 0.4 |
| 11 | 0.066 | $FeCl_3.6H_2O$ | sym DMU* 0.23 g | 1.0 | 230–235 | 2 | 0.4 |
| 12 | " | " | $TMU^1$ 0.31 g | 1.0 | 230–235 | 3 | 0.3 |
| 13 | 0.025 | present in rosin | urea 0.1 g | 1.5 | 230–235 | 2 | 0.4 |
| 14 | " | present in rosin | Ethylene diamine 0.05 g | 1.5 | 230–235 | 2 | 0.4 |
| 15 | 0.003 | present in rosin | urea .05 g | 2.0 | 230–235 | 3 | 2 |
| 16 | 0.025 | rosin as above + $FeCl_3.6H_2O$ | urea .05 g | 2.0 | 230–240 | ½ | 0.25 |
| 17 | " | rosin as above + $FeCl_3.6H_2O$ | " | " | 200–205 | 2 | 0.35 |

*sym dimethyl urea
**0.5% when measured using gas liquid chromatography. (The difference is due to the presence of side products that interfered with UV trace).
$^1$tetramethyl urea
Examples 5 and 9 are comparative examples.

I claim:

1. A process for the disproportionation of rosin acids by heating with a catalyst comprising iodine and an iron compound characterised by the use of ammonia, an ammonium salt or urea, dimethyl urea, tetramethyl urea, ethylene diamine, diethylene triamine, or an alkanolamine as an additional component of the catalyst.

2. A process according to claim 1 wherein the unsaturated acids are in rosin or tall oil as starting material.

3. A process according to claim 1 wherein the rosin acids are mixed with unsaturated fatty acids or polyunsaturated fatty acids or a mixture of unsaturated fatty acids and polyunsaturated fatty acids.

4. A process according to claim 3 wherein the unsaturated acids are a mixture of fatty acids and rosin acids derived from tall oils.

5. A process according to claim 1 wherein there is employed ammonia, ammonia carbonate, ammonium chloride, urea, dimethyl urea, tetramethyl urea, ethylene diamine, diethylene triamine or an alkanolamine.

6. A process according to claim 5 wherein there is employed urea.

7. A process according to claim 1 comprising employing ammonium carbonate as the catalyst and completing the reaction within 15 minutes at a temperature of at least 220° C.

8. A process according to claim 1 wherein the starting material consists essentially of rosin.

* * * * *